US012760239B2

(12) United States Patent
Zha et al.

(10) Patent No.: US 12,760,239 B2
(45) Date of Patent: Oct. 13, 2026

(54) PROCESS FOR ENZYMATIC OIL DEGUMMING INVOLVING PHOSPHOLIPASE A2

(71) Applicant: DSM IP Assets B.V., Heerlen (NL)

(72) Inventors: Ying Zha, Echt (NL); Lambertus Jacobus Otto Guilonard, Echt (NL); Nikita Alexeivich Iltchenko, Echt (NL); Weixi Qiu, Echt (NL)

(73) Assignee: DSM IP Assets B.V., Heerlen (NL)

( * ) Notice: Subject to any disclaimer, the term of this patent is extended or adjusted under 35 U.S.C. 154(b) by 272 days.

(21) Appl. No.: 18/725,597

(22) PCT Filed: Dec. 22, 2022

(86) PCT No.: PCT/EP2022/087453
§ 371 (c)(1),
(2) Date: Jun. 28, 2024

(87) PCT Pub. No.: WO2023/126302
PCT Pub. Date: Jul. 6, 2023

(65) Prior Publication Data
US 2025/0109352 A1 Apr. 3, 2025

(30) Foreign Application Priority Data
Jan. 3, 2022 (EP) .................................... 22150061

(51) Int. Cl.
*C11B 3/00* (2006.01)
*A23D 9/02* (2006.01)
*A23D 9/04* (2006.01)
*C12N 9/18* (2006.01)

(52) U.S. Cl.
CPC ................ *C11B 3/003* (2013.01); *A23D 9/04* (2013.01); *C12N 9/18* (2013.01); *C12Y 301/01004* (2013.01)

(58) Field of Classification Search
None
See application file for complete search history.

(56) References Cited

U.S. PATENT DOCUMENTS 9,670,470 B2 * 6/2017 Borch ..................... C12N 9/20

FOREIGN PATENT DOCUMENTS

EP 869167 B2 10/1998
JP H11228986 A 8/1999
WO 2011101339 A2 8/2011

OTHER PUBLICATIONS

Altschul et al., Basic Local Alignment Search Tool. J Mol Biol. 1990;215(3):403-10.
Altschul et. al., Gapped BLAST and PSI-BLAST: a new generation of protein database search programs. Nucleic Acids Res. 1997;25(17):3389-402.
Needleman et al., A General Method Applicable to the Search for Similarities in the Amino Acid Sequence of Two Proteins. J Mol Biol. 1970;48(3):443-53.
Rice et al., EMBOSS: The European Molecular Biology Open Software Suite. Trends Genet. 2000; 16(6):276-7.
International Search Report and Written Opinion of International Application No. PCT/EP2022/087453, issued Apr. 6, 2023, 14 pages.
Liu et al., "Characterization of the recombinant porcine pancreas phospholipase A2 expressed in Pichia pastoris GS115 and its application to synthesis of 2-DHA-PS", Process Biochemistry, vol. 51, No. 10, Jun. 23, 2016, pp. 1472-1478.
Kuipers et al., "Enhanced activity and altered specificity of phospholipase A2 by deletion of a surface loop", Science, vol. 244, No. 4900, Apr. 7, 1989, pp. 82-85.
Casado et al., "Phospholipases in food industry: a review", Antibody-drug Conjugates, In: Methods in Molecular Biology, Issn: 1064-3745, vol. 263, Lipases and phospholipases: Methods and protocols, vol. 861, 2012, pp. 495-523.
Anonymous: "P00592", XP93034768, Database accession No. PA21B_PIG Sep. 29, 2021.
Puijk et al., "The primary structure of phospholipase A2 from porcine pancreas a reinvestigation", Biochimica et Biophysica Acta (BBA)-Protein Structure, vol. 492, No. 2, Jun. 24, 1977, pp. 254-259.

* cited by examiner

*Primary Examiner* — Manjunath N Rao
*Assistant Examiner* — Jae W Lee
(74) *Attorney, Agent, or Firm* — McBee Moore & Vanik IP, LLC

(57) ABSTRACT

The present invention relates to a process for reducing an amount of phospholipids in an oil composition using an enzyme having phospholipase A2 activity.

11 Claims, No Drawings

Specification includes a Sequence Listing.

PROCESS FOR ENZYMATIC OIL DEGUMMING INVOLVING PHOSPHOLIPASE A2

CROSS-REFERENCE TO RELATED APPLICATIONS

This application is the National Stage entry of International Application No. PCT/EP2022/087453, filed 22 Dec. 2022, which claims priority to European Patent Application No. 22150061.4, filed Jan. 3, 2022.

BACKGROUND

Field

The present invention relates to a process for reducing an amount of phospholipids in an oil composition using an enzyme having phospholipase A2 activity.

Description of Related Art

Vegetable oils, such as oils from soybean, sunflower and rapeseed, must be refined to remove the impurities in order for them to be suitable for direct human consumption. Some of the impurities, such as seed fragments and meal fines, are oil insoluble and thus can be readily removed by filtration. Others, including free fatty acids, hydrocarbons, ketones, tocopherols, glycolipids, phytosterols, phospholipids, proteins, pigments, and resins, are soluble or form stable colloidal suspensions in the oil. Most of these have an unfavourable effect on the flavour, odour, appearance, and/or shelf life of the oil, and therefore have to be removed from the oils by chemical or physical refining processes.

In particular, phospholipids pose many problems for the storage and processing of the crude oil and can be removed from oil by processes such as water or wet degumming, acid degumming, caustic refining and enzymatic degumming or refining.

Various processes are known for enzymatic degumming or enzymatic refining of oils using enzymes such as for example enzymes having phospholipase A1 activity, phospholipase C activity or phosphatidyl inositol phospholipase C activity.

Other enzymes that are present in the market include phospholipase A2. However, phospholipase A2 is mainly produced from porcine pancreas and used for production of lysolecithin, a different application. The use of enzymes produced from porcine pancreas for enzymatic degumming or enzymatic refining of vegetable oils is undesirable. For vegan, kosher and halal customers of vegetable oils the use of such porcine pancreas originating enzyme is simply not acceptable.

JPH1-1228986A describes degumming of fats and oils by using pig pancreas phospholipase A1 and/or A2 that was immobilized by a cation exchanger which consists of a hydrophobic carrier and cation exchange group. However, in addition to the above disadvantages, retrieval of phospholipase from pig pancreas is expensive and immobilization thereof on the described carrier increases costs further. This makes the method of JPH1-1228986A exceptionally expensive.

Despite the progress in enzymatic degumming and enzymatic refining technology, still a need remains in the art to provide improved processes for reducing the content of phospholipids in an oil composition using enzymes.

SUMMARY

The present invention relates to a process for reducing an amount of phospholipids in an oil composition. The process includes contacting the oil composition with a polypeptide having phospholipase A2 activity and water and incubating the oil composition under specific time and temperature conditions.

The invention thus advantageously provides a process for reducing an amount of phospholipids in an oil composition, the process comprising the steps of:

a) providing an oil composition containing an amount of phospholipids,
b) contacting the oil composition with a polypeptide having phospholipase A2 activity and water,
c) incubating the oil composition for 5 to 180 minutes at a temperature of 75° C. to 90° C. to obtain an oil composition having a reduced amount of phospholipids compared to the amount of phospholipids originally present in the oil composition.

The present invention relates to a process for reducing an amount of phospholipids in an oil composition. The process includes contacting the oil composition with a polypeptide having phospholipase A2 activity and water and incubating the oil composition under specific time and temperature conditions.

REFERENCE TO SEQUENCE LISTING SUBMITTED AS A COMPLIANT XML FILE (.xml)

Pursuant to the EFS-Web legal framework and 37 CFR §§ 1.821-825 (see MPEP § 2442.03 (a)), a Sequence Listing in the form of an XML file (entitled "34315-WO-PCT.xml" created on 12 Dec. 2022, and 4,292 bytes in size) is submitted concurrently with the instant application, and the entire contents of the Sequence Listing are incorporated herein by reference.

| SEQ ID NO: | Enzyme Name | Origin | Type |
|---|---|---|---|
| SEQ ID NO: 1 | Mature polypeptide | *Aspergillus niger* | protein |
| SEQ ID NO: 2 | polypeptide having phospholipase A2 activity | *Aspergillus niger* | protein |
| SEQ ID NO: 3 | polypeptide having phospholipase A2 activity | *Aspergillus niger* | protein |

DETAILED DESCRIPTION OF A PREFERRED EMBODIMENT

The present invention relates to a process for reducing an amount of phospholipids in an oil composition, the process comprising the steps of (a) providing an oil composition containing an amount of phospholipids, (b) contacting the oil composition with a polypeptide having phospholipase A2 activity and water, (c) incubating the oil composition for 5 to 180 minutes at a temperature of 75° C. to 90° C. to obtain an oil composition having a reduced amount of phospholipids compared to the amount of phospholipids originally present in the oil composition.

In an embodiment the incubation is done at a temperature of 76° C. to 88° C. In an embodiment the incubation is done at a temperature of 77° C. to 86° C. In an embodiment the incubation is done at a temperature of 78° C. to 84° C. In an embodiment the incubation is done at a temperature of 79° C. to 82° C. In an embodiment the incubation is done at a temperature of about 80° C.

In an embodiment the incubation is done at a pH of 4 to 10. In an embodiment the incubation is done at a pH of 5 to 9. In an embodiment the incubation is done at a pH of 6 to 8. In an embodiment the incubation is done at a pH of about 7.

In an embodiment the incubation is done for 5 to 120 minutes. In an embodiment the incubation is done for 10 to 110 minutes. In an embodiment the incubation is done for 15 to 100 minutes. In an embodiment the incubation is done for 20 to 90 minutes. In an embodiment the incubation is done for 25 to 80 minutes. In an embodiment the incubation is done for 30 to 60 minutes.

In an embodiment the oil composition in step (a) of the process of the present invention comprises a temperature of 75° C. to 90° C. In an embodiment the oil composition comprises a temperature of 76° C. to 88° C. In an embodiment the oil composition comprises a temperature of 77° C. to 86° C. In an embodiment the oil composition comprises a temperature of 78° C. to 84° C. In an embodiment the oil composition comprises a temperature of 79° C. to 82° C. In an embodiment the oil composition comprises a temperature of about 80° C.

In an embodiment the oil composition is not subjected to a cooling step before contacting it with the polypeptide having phospholipase A2 activity and water.

In an embodiment water is added in an amount of 0.1 wt % to 10 wt %. In an embodiment water is added in an amount of 0.5 wt % to 8 wt % (v/v). In an embodiment water is added in an amount of 1 wt % to 6 wt % (v/v). In an embodiment water is added in an amount of 2 wt % to 5 wt % (v/v).

In an embodiment the oil composition, the polypeptide having phospholipase A2 activity and the water are mixed before incubation. Mixing can be done in a static mixer, a high shear mixer, a mixing reactor, to name just a few. In an embodiment the mixing is done in line. In an embodiment the mixing speed is 1,000 rpm to 20,000 rpm. In an embodiment the mixing speed is 2,000 rpm to 15,000 rpm. In an embodiment the mixing speed is 3,000 rpm to 10,000 rpm. In an embodiment the mixing speed is 4,000 rpm to 8,000 rpm. In an embodiment the mixing speed is 5,000 rpm to 6,000 rpm.

In an embodiment the oil composition, the polypeptide having phospholipase A2 activity and the water are agitated during incubation. Agitation can be done by top mixing, pump recirculation, to name just a few.

In an embodiment the polypeptide having phospholipase A2 activity is contacted with the water before it is contacted with the oil composition.

In an embodiment the process of the present invention is free of an emulsification step. An emulsification step as used herein means a process wherein a stable oil/water emulsion is formed. The emulsification step can be performed by means of a high shear mixing. High shear mixing can be done by means of a high shear disperser, a roto/stator homogenizer or any other high shear mixing technology.

In an embodiment the oil composition in step (a) of the process of the present invention comprises 50 ppm or more phosphorous in the form of phospholipids. In an embodiment the oil composition comprises 100 ppm or more phosphorous in the form of phospholipids. In an embodiment the oil composition comprises 200 ppm or more phosphorous in the form of phospholipids. In an embodiment the oil composition comprises 300 ppm or more phosphorous in the form of phospholipids. In an embodiment the oil composition comprises 400 ppm or more phosphorous in the form of phospholipids. In an embodiment the oil composition comprises 500 ppm or more phosphorous in the form of phospholipids. In an embodiment the oil composition comprises 600 ppm or more phosphorous in the form of phospholipids. In an embodiment the oil composition comprises 700 ppm or more phosphorous in the form of phospholipids. In an embodiment the oil composition comprises 800 ppm or more phosphorous in the form of phospholipids. In an embodiment the oil composition comprises 900 ppm or more phosphorous in the form of phospholipids.

In an embodiment the oil composition comprises triglycerides. The wordings "triglyceride" and "triacylglyceride" can be used interchangeably herein. A "triglyceride" as used herein is defined as an ester derived from glycerol and three fatty acids. A triglyceride oil can be an edible oil and/or an oil used as a biodiesel.

In an embodiment the oil composition may comprise an edible oil. The oil composition may comprise a vegetable oil or plant oil, animal oil, fish oil and/or algal oil. A vegetable oil may be any suitable oil for instance a soybean oil, a rapeseed oil, a canola oil, a sunflower oil, a palm oil, a palm kernel oil, a coconut oil, a sesame oil, an olive oil, a rice bran oil, a cotton seed oil, a corn oil, a nuts oil, such as an almond oil, a walnut oil and/or a peanut oil.

In an embodiment the oil composition having a reduced amount of phospholipids comprises triglycerides. In an embodiment the triglycerides have fatty acid elements of different lengths. In an embodiment the oil composition and the oil composition having a reduced amount of phospholipids comprises a mix of various triglycerides. In an embodiment the oil composition and the oil composition having a reduced amount of phospholipids comprises triglycerides with medium to long-chain fatty acids, usually of equal or nearly equal length.

In an embodiment the phospholipids comprise phosphatidic acid, phosphatidyl ethanolamine, phosphatidyl inositol and/or phosphatidylcholine. A phospholipid is also indicated as a glycerophospholipid. A "phospholipid" as used herein is an "intact" phospholipid which comprises a glycerol backbone comprising two fatty acids and a phosphate group. A phospholipid is also indicated as diacylglyceride comprising a phosphate group on the third position.

In an embodiment the process further comprises the step of separating phosphorous-containing components from the oil composition. In an embodiment the separation step is performed after the incubation step. Separating phosphorous-containing components can be performed by any suitable method known in the art for instance by centrifugation or gravity settling.

In an embodiment the process further comprises the step of degumming the oil composition. In an embodiment the process further comprises the step of deep-degumming the oil composition to reach a phosphorous level below 5 ppm. In an embodiment the deep-degumming step is performed after the incubation step. The deep-degumming step may be a chemical deep-degumming step, a physical deep-degumming step, an enzymatic deep-degumming step or any other deep-degumming step that allows to reach a phosphorous level below 5 ppm or any combination of the above.

In an embodiment the oil composition is heated after incubation and before separating phosphorous-containing components from the oil composition. In an embodiment the oil composition is heated after incubation and before separating phosphorous-containing components from the oil composition using mechanical or gravity means. In an embodiment the oil composition is heated to a temperature of from 80° C. to 90° C.

In an embodiment the oil composition comprises crude oil and/or degummed oil. Crude oil, also called non-degummed oil, refers to a pressed or extracted oil without any further treatment.

In an embodiment the polypeptide having phospholipase A2 activity is added in an amount of 10 ppm to 300 ppm. In an embodiment the polypeptide having phospholipase A2 activity is added in an amount of 20 ppm to 250 ppm. In an embodiment the polypeptide having phospholipase A2 activity is added in an amount of 30 ppm to 200 ppm. In an embodiment the polypeptide having phospholipase A2 activity is added in an amount of 40 ppm to 150 ppm. In an embodiment the polypeptide having phospholipase A2 activity is added in an amount of 50 ppm to 100 ppm.

The oil composition can be incubated in the presence of an acid. Accordingly, a process according to the present invention may comprise adding an acid such that the amount of acid in the oil composition is from 100 to 1000 ppm of acid, such as from 200 to 900 ppm of acid, for instance from 300 to 800 ppm of acid, for instance from 400 to 600 ppm of acid. A suitable acid used in a process as disclosed herein may comprise citric acid, phosphoric acid, acetic acid, tartaric acid, and/or succinic acid, and any suitable mixture thereof.

In yet another embodiment, a process as disclosed herein comprises adding a caustic to the oil composition. A suitable caustic may for instance be potassium hydroxide, sodium hydroxide, sodium silicate, sodium carbonate, calcium carbonate, sodium bicarbonate, ammonia, sodium citrate or any suitable combination thereof.

Adding an acid and/or caustic may be performed during any suitable step in a process as disclosed herein. Adding an acid and/or caustic may be performed before, during or after incubating the oil composition with the polypeptide having phospholipase A2 activity.

A "polypeptide having phospholipase A2 activity" as used herein is defined as a polypeptide that releases fatty acids from the second carbon group of glycerol, also called sn-2 position, and belongs to enzyme classification EC 3.1.1.4. Herein below the "polypeptide having phospholipase A2 activity" may also be referred to as "phospholipase A2 enzyme" or simply "phospholipase A2".

A polypeptide having phospholipase A2 activity used in a process as disclosed herein may be a natural occurring polypeptide or a variant polypeptide.

A polypeptide having phospholipase A2 activity may be produced in any suitable host cell useful for producing a polypeptide having phospholipase A2 activity as disclosed herein, for instance a prokaryotic or eukaryotic cell. A eukaryotic host cell may be a mammalian, insect, plant or fungal cell. It is also possible to use a prokaryotic host cell, such as for example a bacterial cell, for example a *Bacillus* strain, such as a *Bacillus subtilis*.

Preferably the host cell is a fungal cell. Preferably the polypeptide having phospholipase A2 activity is thus produced in fungal cell. That is, preferably the polypeptide having phospholipase A2 activity is a polypeptide having phospholipase A2 activity produced in a micro-organism. Such a polypeptide can also be referred to as a microbial polypeptide having phospholipase A2 activity. More preferably the polypeptide having phospholipase A2 activity is a polypeptide having phospholipase A2 activity produced in a fungus. Such a polypeptide can also be referred to as a fungal polypeptide having phospholipase A2 activity. Such preferred microbial, more preferably fungal, polypeptide having phospholipase A2 activity is advantageous as the resulting refined vegetable oils are also acceptable to vegan, kosher and halal customers.

An especially preferred fungus is *Aspergillus niger*. An especially preferred host cell is thus an *Aspergillus niger* cell. Hence, preferably the polypeptide having phospholipase A2 activity is a polypeptide having phospholipase A2 activity produced in *Aspergillus niger*.

A host cell useful for producing a polypeptide having phospholipase A2 activity as disclosed herein is cultivated in a suitable fermentation medium that allows expression of the polypeptide having phospholipase A2 activity. A person skilled in the art knows how to perform a process for preparing a polypeptide having phospholipase A2 activity depending on the host cell used. A suitable fermentation medium usually comprises a carbon and a nitrogen source. Usually, a fermentation medium has a pH value of between 4 and 8. A suitable temperature at which a host cell is cultivated is usually between 25° C. and 60° C. The polypeptide having phospholipase A2 activity can be recovered from the fermentation medium by methods known in the art, for instance by centrifugation, filtration and/or ultrafiltration.

A polypeptide having phospholipase A2 activity in a process as disclosed herein may be a composition comprising the polypeptide having phospholipase A2 activity as disclosed herein, for instance an aqueous composition or a solid composition comprising a polypeptide having phospholipase A2 activity as disclosed herein. A composition may be a fermentation broth, such as a fermentation broth from which cells and/or other components have been removed, for instance by centrifugation, filtration or ultrafiltration.

A polypeptide having phospholipase A2 activity may be a pure or an isolated polypeptide having phospholipase A2 activity, i.e., a polypeptide having phospholipase A2 activity that is removed from at least one component, e.g., other polypeptide material with which it is naturally associated.

In an embodiment the polypeptide having phospholipase A2 activity comprises an amino acid sequence comprising at least 80% identity to the amino acid sequence of SEQ ID NO: 2. In an embodiment the polypeptide having phospholipase A2 activity comprises an amino acid sequence comprising at least 85% identity to the amino acid sequence of SEQ ID NO: 2. In an embodiment the polypeptide having phospholipase A2 activity comprises an amino acid sequence comprising at least 90% identity to the amino acid sequence of SEQ ID NO: 2. In an embodiment the polypeptide having phospholipase A2 activity comprises an amino acid sequence comprising at least 95% identity to the amino acid sequence of SEQ ID NO: 2. Preferably the polypeptide having phospholipase A2 activity comprises an amino acid sequence comprising at least 95%, more preferably at least 98% and most preferably at least 99% identity to the amino acid sequence of SEQ ID NO: 2. In an embodiment the polypeptide having phospholipase A2 activity comprises an amino acid sequence comprising the amino acid sequence of SEQ ID NO: 2.

SEQ ID NO: 2 is the mature polypeptide of the polypeptide comprising SEQ ID NO: 1. A "mature polypeptide" as used herein is defined as a polypeptide in its final form which is obtained after translation of an mRNA into a polypeptide and post-translational modifications of said polypeptide. Post-translational modifications include N-terminal processing, C-terminal truncation, glycosylation, phosphorylation and removal of leader sequences such as signal peptides, propeptides and/or prepropeptides by cleavage.

In an alternative embodiment the polypeptide having phospholipase A2 activity comprises an amino acid sequence comprising at least 80% identity to the amino acid sequence of SEQ ID NO: 3. In an embodiment the polypeptide having phospholipase A2 activity comprises an amino acid sequence comprising at least 85% identity to the amino acid sequence of SEQ ID NO: 3. In an embodiment the polypeptide having phospholipase A2 activity comprises an amino acid sequence comprising at least 90% identity to the amino acid sequence of SEQ ID NO: 3. In an embodiment the polypeptide having phospholipase A2 activity comprises an amino acid sequence comprising at least 95% identity to the amino acid sequence of SEQ ID NO: 3. Preferably the polypeptide having phospholipase A2 activity comprises an amino acid sequence comprising at least 95%, more preferably at least 98% and most preferably at least 99% identity to the amino acid sequence of SEQ ID NO: 3. In an embodiment the polypeptide having phospholipase A2 activity comprises an amino acid sequence comprising the amino acid sequence of SEQ ID NO: 3.

Sequence identity, or sequence homology are used interchangeable herein. In order to determine the percentage of sequence homology or sequence identity of two amino acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region. The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp. 276-277, emboss.bioinformatics.nl/). For protein sequences EBLOSUM62 is used for the substitution matrix. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms. After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest-identity".

The protein sequences disclosed herein can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25 (17): 3389-3402. When utilizing BLAST and Gapped BLAST programs, the default parameters of the respective programs (e.g., XBLAST and NBLAST) can be used. See the homepage of the National Center for Biotechnology Information at www.ncbi.nlm.nih.gov/.

The fungal phospholipase A2 Purifine® currently marketed by DSM Food & Beverages is especially preferred as a polypeptide having phospholipase A2 activity.

The polypeptide having phospholipase A2 activity may or may not comprise one or more isoenzymes. More preferably a polypeptide having phospholipase A2 activity is used which comprises, based on the total weight of all phospholipase A2 isoenzymes present, equal to or more than 80% w/w, more preferably more than 90% w/w, even more preferably equal to or more than 95% w/w, still more preferably equal to or more than 99% w/w, and even still more preferably equal to or more than 99.9% w/w of the isoenzyme PA21B_PIG. Most preferably the polypeptide having phospholipase A2 activity consists essentially or completely of isoenzyme PA21B_PIG. This isoenzyme is also referred to as the "Phospholipase A2, major isoenzyme" (please also note the reference to this isoenzyme on the uniprot website www.uniprot.org as entry "P00592•PA21B_PIG").

Preferably the polypeptide having phospholipase A2 activity is thermostable. However, more preferably the polypeptide having phospholipase A2 activity does have a reduced stability, and more preferably becomes instable or disintegrates, at a temperature of equal to or more than 95° C., more preferably already at a temperature of equal to or more than 90.8° C. Such reduced stability advantageously allows for heating of the oil composition (i.e. the product of the process) at 100° C. to be sufficiently effective to inactivate the enzyme.

Hence, the polypeptide having phospholipase A2 activity is preferably a phospholipase A2 that, in an environment having a pH of 7, after 60 minutes at 90.8° C. has a residual activity (also referred to herein as "remaining activity") of equal to or less than 65%, more preferably equal to or less than 60%, most preferably equal to or less than 55%, of the original activity, wherein such original activity is the activity as determined in the same environment having a pH of 7, after 2 minutes at 50° C. (The original activity at a pH of 7, after 2 minutes at 50° C. is thus set at 100%). Such original, respectively residual, activity can suitably be determined by measuring the Optical Density (OD) at 405 nm with a suitable spectrophotometer, such as a programmed Gallery™ Discrete Analyzer from Thermo Scientific. For the determination of such activity the phospholipase A2 may suitably be stabilized in a buffer of pH 7, wherein such buffer may suitably comprise 200 millimolar (mM) 3-(N-morpholino) propane sulfonic acid (MOPS), 100 millimolar (mM) sodium chloride (NaCl), 15 millimolar (mM) CaCl2 and 0.2% wt/wt t-octylphenoxypolyethoxyethanol (also referred to as polyethylene glycol tert-octylphenyl ether, commercially obtainable as Triton™ X-100 from Sigma Aldrich). The original activity, respectively residual activity, can suitably be determined using the compound rac 1,2-dioctanoyl dithio phosphatidyl choline as a reference substrate. Such is illustrated in the examples.

The polypeptide having phospholipase A2 activity is preferably a phospholipase A2 that, in an environment having a pH of 7, after 60 minutes at 80.7° C. has a residual activity (also referred to herein as "remaining activity") of equal to or more than 75%, more preferably equal to or more than 80%, of the original activity, wherein such original activity is the activity as determined in the same environment having a pH of 7, after 2 minutes at 50° C. (The original activity at a pH of 7, after 2 minutes at 50° C. is thus set at 100%). Such original, respectively residual, activity can suitably be determined by measuring the Optical Density (OD) at 405 nm with a suitable spectrophotometer using a buffer and substrate as described above.

Therefore, the phospholipase A2 is preferably a phospholipase A2 wherein the ratio of residual activity after 60 minutes at pH 7 and 90.8° C. to the residual activity after 60 minutes at pH 7 and 80.7° C., both as determined above, is equal to or less than 0.70.

The polypeptide having phospholipase A2 activity can be mobile or immobile. That is, the polypeptide having phospholipase A2 activity may or may not be fixed or immobilized, for example on a carrier. Preferably the polypeptide having phospholipase A2 activity is mobile. That is, preferably the polypeptide having phospholipase A2 activity is a polypeptide having phospholipase A2 activity is not fixed or immobilized, for example on a carrier. Preferably the polypeptide having phospholipase A2 activity is not used in combination with any cation exchanger, for example a cation exchanger which consists of a hydrophobic carrier and cation exchange group. A mobile, that is not immobilized, polypeptide having phospholipase A2 activity has the advantage that it is cheaper and more easy to use.

In an embodiment the polypeptide having phospholipase A2 activity is capable of reducing at least 10% of the amount of phospholipids originally present in the oil composition, when the polypeptide having phospholipase A2 activity is incubated with the oil composition in an amount of 0.8 mg protein/kg oil composition at a temperature of 80° C. for 1 hr. In an embodiment the polypeptide having phospholipase A2 activity is capable of reducing at least 20% of the amount of phospholipids originally present in the oil composition, when the polypeptide having phospholipase A2 activity is incubated with the oil composition in an amount of 0.8 mg protein/kg oil composition at a temperature of 80° C. for 1 hr. In an embodiment the polypeptide having phospholipase A2 activity is capable of reducing at least 30% of the amount of phospholipids originally present in the oil composition, when the polypeptide having phospholipase A2 activity is incubated with the oil composition in an amount of 0.8 mg protein/kg oil composition at a temperature of 80° C. for 1 hr. In an embodiment the polypeptide having phospholipase A2 activity is capable of reducing at least 40% of the amount of phospholipids originally present in the oil composition, when the polypeptide having phospholipase A2 activity is incubated with the oil composition in an amount of 0.8 mg protein/kg oil composition at a temperature of 80° C. for 1 hr. In an embodiment the polypeptide having phospholipase A2 activity is capable of reducing at least 50% of the amount of phospholipids originally present in the oil composition, when the polypeptide having phospholipase A2 activity is incubated with the oil composition in an amount of 0.8 mg protein/kg oil composition at a temperature of 80° C. for 1 hr. In an embodiment the polypeptide having phospholipase A2 activity is capable of reducing at least 60% of the amount of phospholipids originally present in the oil composition, when the polypeptide having phospholipase A2 activity is incubated with the oil composition in an amount of 0.8 mg protein/kg oil composition at a temperature of 80° C. for 1 hr. In an embodiment the polypeptide having phospholipase A2 activity is capable of reducing at least 70% of the amount of phospholipids originally present in the oil composition, when the polypeptide having phospholipase A2 activity is incubated with the oil composition in an amount of 0.8 mg protein/kg oil composition at a temperature of 80° C. for 1 hr. In an embodiment the polypeptide having phospholipase A2 activity is capable of reducing at least 80% of the amount of phospholipids originally present in the oil composition, when the polypeptide having phospholipase A2 activity is incubated with the oil composition in an amount of 0.8 mg protein/kg oil composition at a temperature of 80° C. for 1 hr.

Phosphorous components such as phospholipids, lysophospholipids and phosphate esters can be determined using $^{31}$P-NMR and/or HPLC for instance as described below.

Weigh 500-1000 mg oil accurately into a suitable vial and add approximately 10 g cold acetone and mix thoroughly. Keep the oil-acetone mixture at 4° C. for at least 30 minutes. Then centrifuge for 10 minutes at 3000 rpm. Thereafter, discard the liquid phase. Resuspend the pellet in 500 μl buffer (containing 25 g L−1 deoxycholic acid, 5.84 g L−1 EDTA, and 10.9 g L−1 TRIS, buffered using KOH at pH 9.0) and add 50 μL of an internal standard solution (containing 10 g L−1 triisopropylphosphate in extraction buffer). Record 1D $P^{31}$ NMR spectra on a Bruker Avance III HD spectrometer, operating at a 31P frequency of 161.97 MHz equipped with a nitrogen cooled cryoprobe, at sample temperature of 300K. Use an inverse gated pulse program (ZGIG) with Waltz16 proton decoupling, recording 4 dummy scans, and 128 scans per spectrum, using a 90-degree pulse. Use an acquisition time of 3.37 seconds and a relaxation delay of 11.5 seconds. Calculate the analyte concentrations relative to triisopropylphosphate. Apply a correction factor to correct for the incomplete relaxation of cholinephosphate and ethanolaminephosphate.

In one embodiment a process as disclosed herein further comprises incubating the oil composition with a polypeptide having phospholipase A1 activity, a polypeptide having phosphatidylinositol phospholipase C (PI-PLC) activity and/or a polypeptide having phospholipase C activity.

In an embodiment the oil composition or the oil composition having a reduced amount of phospholipids is incubated with a polypeptide having phospholipase A1 activity. A "polypeptide having phospholipase A1 activity" as used herein is defined as a polypeptide that belongs to enzyme classification E.C. 3.1.1.32. A "polypeptide having phospholipase A1 activity" as used herein is an enzyme that cleaves a phospholipid at the SN1 position forming a lysophospholipid and a fatty acid. A "polypeptide having phospholipase A1 activity" as used herein may also cleave a lysophospholipid at the SN1 position forming a glycerophosphate and a fatty acid. A polypeptide having phospholipase A1 activity as disclosed herein preferably does not have phospholipase A2 activity.

In an embodiment the oil composition or the oil composition having a reduced amount of phospholipids is incubated with a polypeptide having phospholipase C activity. A "polypeptide having phospholipase C activity" as used herein is defined as a polypeptide that belongs to enzyme classification number EC 3.1.4.3 and that cleaves phospholipids between the phosphate and the glycerol group, resulting in a diglyceride and a phosphate compound such as choline phosphate or ethanolamine phosphate.

In an embodiment the oil composition or the oil composition having a reduced amount of phospholipids is incubated with a polypeptide having phosphatidylinositol phospholipase C (PI-PLC) activity. A "polypeptide having phosphatidylinositol phospholipase C (PI-PLC) activity" as used herein is defined as a polypeptide that has a preference of cleaving phosphatidylinositol and may also act on other phospholipids such as phosphatidylcholine and phosphatidylethanolamine. Bacterial PI-PLC belongs to enzyme classification EC 4.6.1.13.

The present invention also pertains to an oil composition comprising a polypeptide having phospholipase A2 activity which comprises an amino acid sequence comprising at least 80% identity, preferably at least 90% identity, more preferably at least 95% identity, and most preferably at least 99% identity, to the amino acid sequence of SEQ ID NO: 2. All features and embodiments described for the process of the present invention also apply to the oil compositions according to the present invention.

The present invention also pertains to an oil composition comprising a polypeptide having phospholipase A2 activity which comprises an amino acid sequence comprising at least 80% identity, preferably at least 90% identity, more preferably at least 95% identity, and most preferably at least 99% identity, to the amino acid sequence of SEQ ID NO: 3. All features and embodiments described for the process of the present invention also apply to the oil compositions according to the present invention.

Example 1

Reduction of Phospholipids in Soybean Oil and Rapeseed Oil Using Phospholipase A2

Phospholipids were reduced in three different oils using phospholipase A2 (PLA2). This PLA2 was a fungal, i.e. a microbial, PLA2.

The three different oils tested were:

- A rapeseed oil from Germany containing 2.23% w/w phospholipids,
- A soybean oil from Brazil containing 0.88% w/w phospholipids, and
- A soybean oil from Uruguay containing 1.54% w/w phospholipids.

10 g of each oil was weighed into a vial and heated to 80° C., after which 3% water and 80 ppm of a polypeptide having phospholipase A2 activity comprising the amino acid sequence of SEQ ID NO: 2 were added to obtain oil mixtures.

The oil mixture comprising the soybean oil from Brazil was high shear mixed with a IKA® ULTRA-TURRAX® Tube Drive system at 6000 RPM for 20 seconds.

Next, all oil mixtures were stirred with magnetic stirring at 150 rpm at 80° C. for 3 hours with samples removed at 0.5, 1 and 3 hours for phospholipid (PL), lysophospholipid (LPL) and glycerophosphate (GPL) content analysis, e.g., phosphatidic acid (PA), phosphatidyl choline (PC), phosphatidyl ethanolamine (PE), and phosphatidyl inositol (PI), using $^{31}$P-NMR as described above.

The results from the content analysis are shown in Tables 1 to 3. In all cases, a reduction in phospholipid content of >50% was observed after 0.5 hour or 1 hour of reaction time. The majority of the converted phospholipid residues was present as lysophospholipid.

Upfront high shear mixing for emulsification purposes did not impact efficacy of the enzyme reaction. Therefore, it can be concluded that the process can be conducted free of an emulsification step.

Example 2

Oil Yield Gain of Crude Soybean Oil Degumming Using Phospholipase A2

2 kg of crude soybean oil was divided into 4 bottles, each bottle containing 400 g of crude soybean oil. The bottles containing oil were heated to 80° C. Then, 5% w/w water together with 50 ppm, 75 ppm or 100 ppm of a polypeptide having phospholipase A2 activity comprising the amino acid sequence of SEQ ID NO: 2 (PLA2) were added into the oils, followed by high-speed mixing at 12,000 rpm for 20 seconds. This PLA2 was a fungal, i.e. a microbial, PLA2. After high-speed mixing, the oil-water-enzyme mixture was incubated for 50 minutes under agitation at 600 rpm. The temperature was kept at 80° C. during the entire process.

After the incubation, the oil-water-enzyme mixture were subjected to a centrifugation step at 4415×g for 10 minutes at 80° C. This step separated the oil phase from the heavy phase containing wet gums. The oil phase and the gum phase were separately collected and weighed. The water and oil content in the gum phase were analysed and the results are shown in Table 4.

The results demonstrate the positive effect of phospholipase A2 treatment on oil yield after gum separation. The experiments with phospholipase A2 incubation resulted in a yield increase of 1.5-1.9% compared to experiment without enzyme addition.

TABLE 1

Phospholipid, lysophospholipid and glycerophosphate content in Brazilian soybean oil, before and after treatment with phospholipase A2, with and without high shear mixing.

| Reaction time [h] | High shear mixing upfront | PA (g/kg) | PC (g/kg) | PE (g/kg) | PI (g/kg) | Total P (g/kg) | Total PL (g/kg) | Total LPL (g/kg) | Total GPL (g/kg) |
|---|---|---|---|---|---|---|---|---|---|
| 0 | — | 0.31 | 0.14 | 0.18 | 0.26 | 1.09 | 0.88 | 0.11 | 0.05 |
| 0.5 | No | 0.12 | 0.06 | 0.09 | 0.13 | 0.62 | 0.39 | 0.16 | 0.04 |
| 1 | No | 0.11 | 0.05 | 0.11 | 0.14 | 0.73 | 0.41 | 0.23 | 0.05 |
| 3 | No | 0.08 | 0.04 | 0.11 | 0.14 | 0.78 | 0.37 | 0.30 | 0.06 |
| 1 | Yes | 0.11 | 0.05 | 0.09 | 0.11 | 0.65 | 0.36 | 0.20 | 0.04 |
| 3 | Yes | 0.08 | 0.06 | 0.13 | 0.18 | 0.90 | 0.45 | 0.34 | 0.07 |

TABLE 2

Phospholipid, lysophospholipid and glycerophosphate content in Uruguayan soybean oil, before and after treatment with PLA2 enzyme.

| Reaction time [h] | High shear mixing upfront | PA (g/kg) | PC (g/kg) | PE (g/kg) | PI (g/kg) | Total P (g/kg) | Total PL (g/kg) | Total LPL (g/kg) | Total GPL (g/kg) |
|---|---|---|---|---|---|---|---|---|---|
| 0 | — | 0.32 | 0.51 | 0.36 | 0.34 | 1.68 | 1.54 | 0.13 | 0.00 |
| 0.5 | No | 0.09 | 0.24 | 0.06 | 0.23 | 1.11 | 0.62 | 0.48 | 0.00 |
| 1 | No | 0.08 | 0.23 | 0.06 | 0.25 | 1.24 | 0.63 | 0.58 | 0.03 |
| 3 | No | 0.07 | 0.15 | 0.09 | 0.20 | 1.13 | 0.51 | 0.59 | 0.01 |

TABLE 3

Phospholipid, lysophospholipid and glycerophosphate content in German rapeseed oil, before and after treatment with PLA2 enzyme.

| Reaction time [h] | High shear mixing upfront | PA (g/kg) | PC (g/kg) | PE (g/kg) | PI (g/kg) | Total P (g/kg) | Total PL (g/kg) | Total LPL (g/kg) | Total GPL (g/kg) |
|---|---|---|---|---|---|---|---|---|---|
| 0 | — | 0.21 | 0.75 | 0.65 | 0.61 | 3.13 | 2.23 | 0.86 | 0.04 |
| 1 | No | 0.05 | 0.46 | 0.40 | 0.45 | 2.54 | 1.35 | 1.14 | 0.03 |
| 3 | No | 0.04 | 0.49 | 0.43 | 0.45 | 2.89 | 1.40 | 1.43 | 0.04 |

TABLE 4

Oil yield gain of crude soybean oil degumming using phospholipase A2.

| Bottle | Crude oil (g) | Water (g) | PLA2 (ppm) | Water phase collected (g) | Gum phase collected (g) | Water content in (g) | Oil content in gum phase (g) | Oil yield after centrifugation (%) | Oil yield increase (%) |
|---|---|---|---|---|---|---|---|---|---|
| 1 | 400 | 20 | 0 | 378.0 | 33.8 | 56.4 | 32.5 | 94.5% | — |
| 2 | 400 | 20 | 50 | 383.8 | 29.2 | 60.1 | 28.1 | 96.0% | 1.5% |
| 3 | 400 | 20 | 75 | 385.8 | 29.0 | 63.3 | 25.9 | 96.4% | 1.9% |
| 4 | 400 | 20 | 100 | 384.9 | 29.2 | 62.9 | 24.8 | 96.2% | 1.7% |

Example 3

Determination of Temperature Profiles of Different Types of Phospholipase A2

A buffer composition of pH 7 was prepared comprising 200 millimolar (mM) 3-(N-morpholino) propane sulfonic acid (MOPS), 100 millimolar (mM) sodiumchloride (NaCl), 15 millimolar (mM) calcium chloride ($CaCl_2$)) and 0.2% wt/wt t-octylphenoxypolyethoxyethanol (also referred to as polyethylene glycol tert-octylphenyl ether, commercially obtainable as Triton™ X-100 from Sigma Aldrich).

Samples of fungal phospholipase A2 enzyme Purifine® LM (commercially obtainable from DSM Food Specialties B.V. Delft, the Netherlands) were diluted in the pH 7 buffer to a concentration that gave a response of approximately 0.08 ΔOD/min in an assay as described below, where Optical Density (OD) was determined at 405 nm as determined with a spectrophotometer, i.e. a programmed Gallery™ Discrete Analyzer from Thermo Scientific.

Subsequently these enzyme solutions were exposed to different temperatures in the range 50-100° C. during different time frames (0 minutes, 2 minutes, 5 minutes, 15 minutes, 30 minutes and 60 minutes) as listed in table 5 below. Afterwards the samples were stored immediately on ice.

Assay to Determine (Remaining) Activity:

Activity was measured using the compound rac 1,2-dioctanoyl dithio phosphatidyl choline (obtained from Symeres, Groningen, The Netherlands) as substrate.

The following solutions were prepared prior to analysis:

1. 0.37 millimolar (mM) rac 1,2-dioctanoyl dithio phosphatidyl choline in a buffer at pH 8.3, wherein the buffer contained 200 millimolar (mM) Tris(hydroxymethyl) aminomethane (TRIS buffer, commercially obtainable from Sigma Aldrich), 100 millimolar (mM) sodium chloride (NaCl), 15 millimolar (mM) calcium chloride ($CaCl_2$)), 1.2 gram/liter (g/l) sodium deoxycholate and 0.2% wt/wt triton X-100
2. Solution of 5.5-dithiobis-2-nitrobenzoïc acid (Sigma D8130) 5 milligram/millilitre (mg/mL) in ethanol. Just before use this solution was diluted in ratio 1:1 (v/v) with the same buffer as described under point 1.
3. Enzyme samples in the buffer of pH 7.0 as described above, which were exposed to the above listed different temperatures during the above listed time (see also table 5 below).

To 200 microliter (μL) of solution 1, which was equilibrated at 37° C., were added as follows:

7 μL of solution 2 and

12 μL of the enzyme sample that was retrieved from the ice.

Immediately after mixing the OD at 405 nm was monitored for 5 minutes. The slope of the linear part of the curve was used as measure of the residual activity.

Results

The activity at the time of 2 minutes at 50° C. was taken as the "original activity" and listed in table 5 below as 100%. The activity as determined for each temperature at a time of 2 minutes, 5 minutes, 15 minutes, 30 minutes and 60 minutes, was compared against this original activity and expressed as a percentage thereof (i.e. herein also referred to as the "residual activity" or the "remaining activity"). The values obtained are listed below in table 5 for fungal phospholipase A2, Purifine® LM.

TABLE 5

Remaining activity of fungal phospholipase A2, Purifin ® LM (PLA2) at a pH of 7

| | Remaining activity @ pH 7 Time [min] | | | | |
|---|---|---|---|---|---|
| Temperature (° C.) | 2 min | 5 min | 15 min | 30 min | 60 min |
| 50.0 | 100% | 96% | 96% | 93% | 93% |
| 54.5 | 101% | 96% | 95% | 94% | 93% |
| 59.1 | 102% | 96% | 95% | 93% | 93% |

TABLE 5-continued

Remaining activity of fungal phospholipase A2, Purifin ® LM (PLA2) at a pH of 7

| | Remaining activity @ pH 7 Time [min] | | | | |
|---|---|---|---|---|---|
| Temperature (° C.) | 2 min | 5 min | 15 min | 30 min | 60 min |
| 64.6 | 104% | 96% | 96% | 94% | 94% |
| 69.3 | 101% | 97% | 96% | 95% | 94% |
| 74.0 | 97% | 97% | 97% | 97% | 96% |
| 80.7 | 96% | 95% | 92% | 89% | 84% |
| 85.4 | 96% | 94% | 87% | 81% | 73% |
| 90.8 | 94% | 91% | 78% | 66% | 54% |

As illustrated by table 5 above, the fungal phospholipase A2, Purifine® LM, performs well at higher temperatures, such as 80.7° C. However, advantageously, at 90.8° C., the remaining activity (also referred to as residual activity) of the fungal phospholipase A2 enzyme, Purifine® LM decreases quickly to a value of 54%.

High residual activity above 90° C. is undesired. After treatment of the oil the enzyme needs to be deactivated again. This is normally done by heating of the oil composition (i.e. the product of the process) at 100° C. The residual activity above 90° is therefore preferably as low as possible.

SEQUENCE LISTING

```
Sequence total quantity: 3
SEQ ID NO: 1           moltype = AA  length = 655
FEATURE                Location/Qualifiers
source                 1..655
                       mol_type = protein
                       organism = Aspergillus niger
SEQUENCE: 1
MSFRSLLALS GLVCTGLANV ISKRATLDSW LSNEATVART AILNNIGADG AWVSGADSGI  60
VVASPSTDNP DYFYTWTRDS GLVLKTLVDL FRNGDTSLLS TIENYISAQA IVQGISNPSG  120
DLSSGAGLGE PKFNVDETAY TGSWGRPQRD GPALRATAMI GFGQWLLDNG YTSTATDIVW  180
PLVRNDLSYV AQYWNQTGYD LWEEVNGSSF FTIAVQHRAL VEGSAFATAV GSSCSWCDSQ  240
APEILCYLQS FWTGSFILAN FDSSRSGKDA NTLLGSIHTF DPEAACDDST FQPCSPRALA  300
NHKEVVDSFR SIYTLNDGLS DSEAVAVGRY PEDTYYNGNP WFLCTLAAAE QLYDALYQWD  360
KQGSLEVTDV SLDFFKALYS DAATGTYSSS SSTYSSIVDA VKTFADGFVS IVETHAASNG  420
SMSEQYDKSD GEQLSARDLT WSYAALLTAN NRRNSVVPAS WGETSASSVP GTCAATSAIG  480
TYSSVTVTSW PSIVATGGTT TTATPTGSGS VTSTSKTTAT ASKRQEGISS RALWQFRSMI  540
KCAIPGSHPL MDFNNYGCYC GLGGSGTPVD ELDRCCETHD NCYRDAKNLD SCKFLVDNPY  600
TESYSYSCSN TEITCNSKNN ACEAFICNCD RNAAICFSKA PYNKEHKNLD TKKYC       655

SEQ ID NO: 2           moltype = AA  length = 121
FEATURE                Location/Qualifiers
source                 1..121
                       mol_type = protein
                       organism = Aspergillus niger
SEQUENCE: 2
QFRSMIKCAI PGSHPLMDFN NYGCYCGLGG SGTPVDELDR CCETHDNCYR DAKNLDSCKF  60
LVDNPYTESY SYSCSNTEIT CNSKNNACEA FICNCDRNAA ICFSKAPYNK EHKNLDTKKY  120
C                                                                 121

SEQ ID NO: 3           moltype = AA  length = 124
FEATURE                Location/Qualifiers
source                 1..124
                       mol_type = protein
                       organism = Aspergillus niger
SEQUENCE: 3
ALWQFRSMIK CAIPGSHPLM DFNNYGCYCG LGGSGTPVDE LDRCCETHDN CYRDAKNLDS  60
CKFLVDNPYT ESYSYSCSNT EITCNSKNNA CEAFICNCDR NAAICFSKAP YNKEHKNLDT  120
KKYC                                                              124
```

The invention claimed is:

1. A process for reducing an amount of phospholipids in an oil composition, the process comprising:

a) providing an oil composition containing an original amount of phospholipids, b) contacting the oil composition with a polypeptide having phospholipase A2 activity and water, c) incubating the oil composition for 5 to 180 minutes at a temperature of 75° C. to 90° C. to obtain an oil composition having a reduced amount of phospholipids compared to the original amount of phospholipids present in the oil composition wherein:

the polypeptide having phospholipase A2 activity comprises an amino acid sequence comprising at least 80% identity to the amino acid sequence of SEQ ID NO:2; and the process is free of emulsification.

2. The process of claim 1, wherein the oil composition in (a) comprises a temperature of 75° C. to 90° C.

3. The process of claim 1, wherein the oil composition in (a) comprises 50 ppm or more phosphorous.

4. The process of claim 1, wherein the polypeptide having phospholipase A2 activity is added in an amount of 10 ppm to 300 ppm.

5. The process of claim 1, wherein the oil composition comprises triglycerides.

6. The process of claim 1, wherein the phospholipids comprise phosphatidic acid, phosphatidyl ethanolamine, phosphatidyl inositol and/or phosphatidylcholine.

7. The process of claim 1, wherein the process further comprises the step of separating phosphorous-containing components from the oil composition.

8. The process of claim 1, wherein the process further comprises the step of degumming the oil composition.

9. The process of claim 1, wherein the oil composition comprises crude oil and/or degummed oil.

10. The process of claim 1, wherein the oil composition is not subjected to cooling before contacting the oil composition with the polypeptide having phospholipase A2 activity and water.

11. The process of claim 1, wherein the polypeptide having phospholipase A2 activity is capable of reducing at least 10% of the amount of phospholipids originally present in the oil composition, when the polypeptide having phospholipase A2 activity is incubated with the oil composition in an amount of 0.8 mg protein/kg oil composition at a temperature of 80° C. for 1 hr.

* * * * *